US00PP34574P2

(12) United States Plant Patent
Graff

(10) Patent No.: US PP34,574 P2
(45) Date of Patent: Sep. 13, 2022

(54) POINSETTIA PLANT NAMED 'QS44'

(50) Latin Name: ***Euphorbia pulcherrima* Willd.**
Varietal Denomination: QS44

(71) Applicant: Poul Graff, Sabro (DK)

(72) Inventor: Poul Graff, Sabro (DK)

(73) Assignee: GRAFF BREEDING A/S, Sabro (DK)

( * ) Notice: Subject to any disclaimer, the term of this patent is extended or adjusted under 35 U.S.C. 154(b) by 0 days.

(21) Appl. No.: 17/694,351

(22) Filed: Mar. 14, 2022

(51) Int. Cl.
*A01H 5/02* (2018.01)
*A01H 6/38* (2018.01)

(52) U.S. Cl.
USPC ..... Plt./307
CPC ..... *A01H 6/385* (2018.05)

(58) Field of Classification Search
USPC ..... Plt./307
CPC ..... A01H 6/385; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of Poinsettia plant named 'QS44', characterized by its compact, upright and uniformly mounding plant habit; moderately vigorous to vigorous growth habit; freely branching habit; dark green-colored leaves; large and full inflorescences with numerous vivid red-colored flower bracts; and excellent post-production longevity.

1 Drawing Sheet

Botanical designation: *Euphorbia pulcherrima* Willd.
Cultivar denomination: 'QS44'.

STATEMENT REGARDING PRIOR DISCLOSURES BY INVENTOR/APPLICANT & ASSIGNEE

An European Community Plant Breeder's Rights application for the instant plant was filed by the Applicant/Assignee of the instant application, Graff Breeding A/S of Sabro, Denmark on Nov. 26, 2021, application number 2021/3054. Foreign priority is not claimed to this European Plant Breeder's Rights application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of Poinsettia plant, botanically known as *Euphorbia pulcherrima* Willd. and hereinafter referred to by the name 'QS44'.

The new Poinsettia plant is a product of a planned breeding program conducted by the Inventor in Sabro, Denmark The objective of the breeding program is to create uniform and freely-branching Poinsettia plants with attractive inflorescences and good postproduction longevity.

The new Poinsettia plant originated from an open-pollination in August, 2018 in Sabro, Denmark of a proprietary selection of *Euphorbia pulcherrima* Willd. identified as code number QA-1177, not patented, as the female, or seed, parent with unknown selection of *Euphorbia pulcherrima* Willd. as the male, or pollen, parent. The new Poinsettia plant was discovered and selected by the Inventor as a single flowering plant within the progeny of the stated open-pollination in a controlled greenhouse environment in Sabro, Denmark in May, 2019.

Asexual reproduction of the new Poinsettia plant by terminal vegetative cuttings in a controlled greenhouse environment in Sabro, Denmark since September, 2019 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'QS44'. These characteristics in combination distinguish 'QS44' as a new and distinct Poinsettia plant:

1. Compact, upright and uniformly mounding plant habit.
2. Moderately vigorous to vigorous growth habit.
3. Freely branching habit.
4. Dark green-colored leaves.
5. Large and full inflorescences with numerous vivid red-colored flower bracts.
6. Excellent post-production longevity.

Plants of the new Poinsettia can be compared to plants of the female parent selection. In side-by-side comparisons, plants of the new Poinsettia differ primarily from plants of the female parent selection in flower bract color as flower bracts of plants of the new Poinsettia are lighter red in color than flower bracts of plants of the female parent selection.

Plants of the new Poinsettia can also be compared to plants of *Euphorbia pulcherrima* Willd. 'NPCW10164', disclosed in U.S. Plant Pat. No. 22,597. In side-by-side comparisons, plants of the new Poinsettia differ primarily from plants of 'NPCW10164' in the following characteristics:

1. Plants of the new Poinsettia are more freely branching than plants of 'NPCW10164'.
2. Flower bracts of plants of the new Poinsettia are slightly shorter than flower bracts of plants of 'NPCW10164'.
3. Flower bracts of plants of the new Poinsettia are lighter in color than flower bracts of plants of 'NPCW10164'.

BRIEF DESCRIPTION OF THE PHOTOGRAPH

The accompanying photograph illustrates the overall appearance of the new Poinsettia plant showing the colors as true as it is reasonably possible to obtain in colored reproductions of this type. Colors in the photograph may differ slightly from the color values cited in the detailed botanical description which accurately describe the colors of the new Poinsettia plant. The photograph is a side perspective view of a typical flowering plant of 'QS44' grown in a container.

DETAILED BOTANICAL DESCRIPTION

The aforementioned photograph and following observations, measurements and values describe plants grown during the winter in 13-cm containers in a glass-covered greenhouse in Sabro, Denmark and under cultural practices typical of commercial Poinsettia production. During the production of the plants, day temperatures averaged 18° C., night temperatures ranged from 16° C. to 18° C. and light levels ranged from 40 to 50 klux. Plants were pinched one time eight weeks after planting and plants were 25 weeks old when the photograph and the description were taken. In the description, color references are made to The Royal Horticultural Society Colour Chart, 2001 Edition, except where general terms of ordinary dictionary significance are used.

Botanical classification: *Euphorbia pulcherrima* Willd. 'QS44'.

Parentage:

*Female, or seed, parent*.—Proprietary selection of *Euphorbia pulcherrima* Willd. identified as code number QS-1177, not patented.

*Male, or pollen, parent*.—Unknown selection of *Euphorbia pulcherrima* Willd., not patented.

Propagation:

*Type*.—Terminal vegetative cuttings.

*Time to initiate roots, summer*.—About three weeks at ambient and substrate temperatures about 24° C.

*Time to initiate roots, winter*.—About four weeks at ambient and substrate temperatures about 24° C.

*Time to produce a rooted young plant, summer*.—About eight weeks at ambient and substrate temperatures about 24° C.

*Time to produce a rooted young plant, winter*.—About ten weeks at ambient and substrate temperatures about 24° C.

*Root description*.—Medium in thickness, fleshy; color, close to 161D, actual color of the roots is dependent on substrate composition, water quality, fertilizer type and formulation, substrate temperature and physiological age of roots.

*Rooting habit*.—Freely branching; dense.

Plant description:

*Plant and growth habit*.—Compact, upright and uniformly mounded plant habit; inverted triangle with rounded crown; large full inflorescences positioned above the foliar plane; moderately vigorous to vigorous growth habit and moderate growth rate.

*Plant height, soil level to top of foliar plane*.—About 15 cm to 25 cm.

*Plant height, soil level to top of floral plane*.—About 20 cm to 30 cm.

*Plant diameter or spread*.—About 30 cm to 45 cm.

*Lateral branch description*.—Branching habit: Freely branching habit, about three to six lateral branches develop after pinching. Length: About 15 cm to 25 cm. Diameter: About 3 mm to 6 mm. Internode length: About 1 cm to 5 cm. Strength: Strong. Texture and luster: Smooth, glabrous; semi-glossy; becoming woody with subsequent development. Angle: Mostly upright to outwardly slanted. Color, developing: Close to 138A. Color, developed: Close to 146A; when woody, becoming closer to 197A.

*Leaf description*.—Arrangement and appearance: Alternate, simple. Length: About 7 cm to 12 cm. Width: About 6 cm to 8 cm. Shape: Broadly ovate. Apex: Acuminate. Base: Rounded. Margin: Entire, moderately and shallowly lobed. Venation pattern: Pinnate, reticulate. Texture and luster, upper and lower surfaces: Rugose, glabrous; leathery; matte. Color: Developing leaves, upper surface: Close to 135B. Developing leaves, lower surface: Close to 137C. Fully expanded leaves, upper surface: Close to N189A; venation, close to 184B. Fully expanded leaves, lower surface: Close to 137B; venation, close to 181D. Petioles: Length: About 3 cm to 8 cm. Diameter: About 3 mm to 5 mm. Strength: Strong. Texture and luster, upper and lower surfaces: Smooth, glabrous; semi-glossy. Color, upper surface: Close to 185A. Color, lower surface: Close to 178A.

Inflorescence description:

*Inflorescence type and habit*.—Large inflorescences are compound corymbs of cyathia with vivid red-colored flower bracts subtending the cyathia; one inflorescence per lateral branch with inflorescences positioned above and beyond the foliar plane.

*Fragrance*.—None detected.

*Natural flowering season*.—Plants flower naturally during the autumn and winter under long nyctoperiod conditions; inflorescence initiation and development can be induced under artificial long nyctoperiod conditions; early flowering habit, response time is about eight weeks after start of long nyctoperiod conditions.

*Post-production longevity*.—Excellent post-production longevity; plants of the new Poinsettia maintain good substance and bract color for about eight to ten weeks under interior conditions; flower bracts persistent.

*Inflorescence diameter* (*including flower bracts*).—About 18 cm to 28 cm.

*Inflorescence height* (*including flower bracts*).—About 5 cm to 7 cm.

*Flower bracts*.—Quantity per inflorescence: About 15 to 25. Length: About 9 cm to 12 cm. Width: About 7 cm to 9 cm. Shape: Ovate. Apex: Acuminate. Base: Obtuse, rounded. Margin: Entire. Venation: Pinnate. Texture and luster, upper and lower surfaces: Rugose, glabrous; matte. Aspect: Mostly horizontal to slightly drooping. Color: Developing bracts, upper surface: Close to 144A. Developing bracts, lower surface: Close to 146C. Transitional bracts, upper surface: Close to 187A, 187B and 187C. Transitional bracts, lower surface: Close to 191A and 187C. Fully expanded bracts, upper surface: Close to 45A; color does not change with subsequent development. Fully expanded bracts, lower surface: Close to 47A; color does not change with subsequent development. Flower bract petioles: Length: About 2 cm to 3 cm. Diameter: About 3 mm to 5 mm. Texture, upper and lower surfaces: Smooth, glabrous. Color, upper surface: Close to 185A. Color, lower surface: Close to 184A.

*Cyathia*.—Quantity per corymb: About 8 to 15. Length: About 5 mm to 10 mm. Width: About 4 mm to 6 mm. Shape: Rounded to ovate. Texture, inner and outer surfaces: Smooth, glabrous. Color, developing, inner surface: Close to 144B. Color, developing, outer surface: Close to 144A. Color, fully developed, inner surface: Close to 144B. Color, fully developed, outer surface: Close to 144A and towards the apex, close to N34A. Nectaries: Quantity per cyathium: If present, typically one. Length: About 3 mm to 5 mm. Diameter: About 3 mm to 6 mm. Shape: Fan-shaped. Texture, inner and outer surfaces: Smooth, glabrous. Color: When developing, inner surface: Close to 151B. When developing, outer surface: Close to 144B. Fully developed, inner surface: Close to 151B. Fully developed, outer surface: Close to 17A.

*Peduncles*.—Length: About 3 mm to 5 mm. Diameter: About 2 mm to 5 mm. Strength: Strong. Aspect: Mostly upright. Texture and luster: Smooth, glabrous; semi-glossy. Color: Close to 138B.

*Reproductive organs*.—Stamens: Quantity per cyathium: About 50. Filament length: About 1 mm to 5 mm. Filament color: Close to 200A. Anther shape: Reniform. Anther length: About 1 mm. Anther color: Close to 187B. Amount of pollen: Abundant. Pollen color: Close to 13B. Pistils: Quantity: Typically one. Pistil length: About 5 mm to 15 mm. Style length: About 1 mm to 3 mm. Style color: Close to 187C. Stigma diameter: About 3 mm. Stigma shape: Star-shaped. Stigma color: Close to 187A. Ovary color: Close to 137A.

*Seeds and fruits*.—To date, seed and fruit development has not been observed on plants of the new Poinsettia.

Pathogen & pest resistance: To date, plants of the new Poinsettia have not been shown to be resistant to pathogens and pests common to Poinsettia plants.

Temperature tolerance: Plants of the new Poinsettia have been observed to tolerate temperatures ranging from about 12° C. to about 35° C.

It is claimed:

1. A new and distinct Poinsettia plant named 'QS44' as illustrated and described.

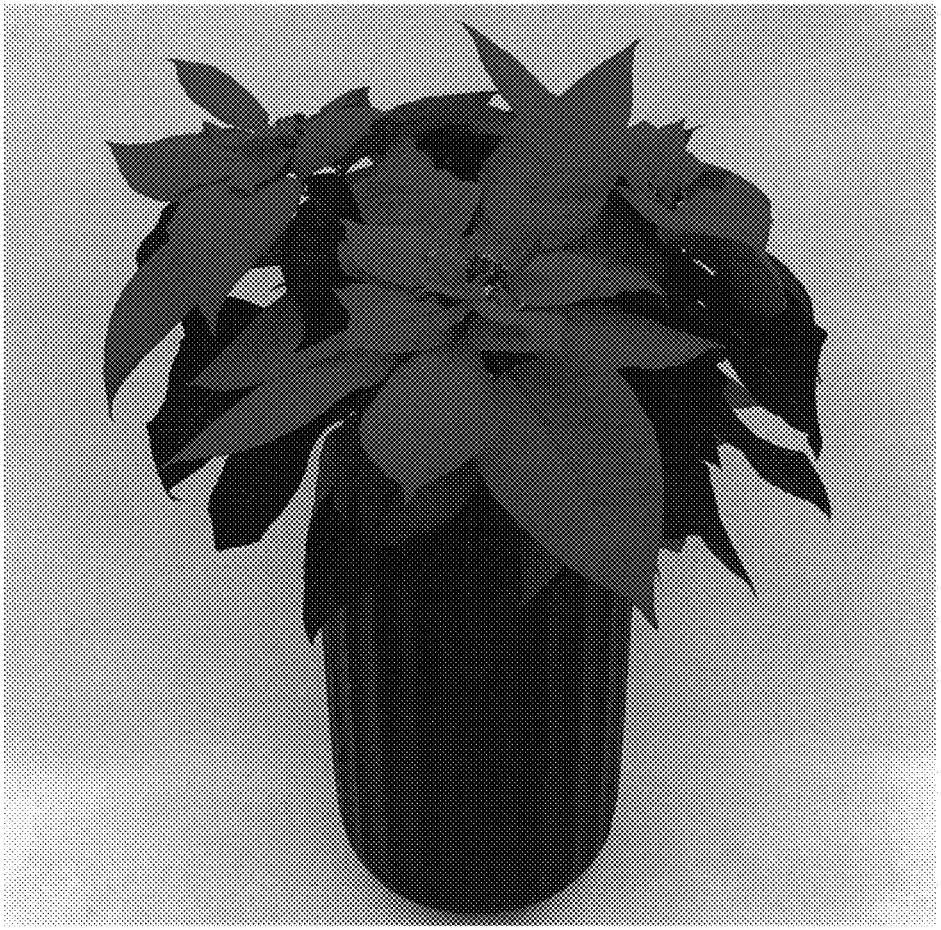

* * * * *